United States Patent [19]

Rothman et al.

[11] Patent Number: 5,047,249
[45] Date of Patent: Sep. 10, 1991

[54] COMPOSITIONS AND METHODS FOR TREATING SKIN CONDITIONS AND PROMOTING WOUND HEALING

[75] Inventors: John Rothman, Lebanon, N.J.; Philip A. Band, Brooklyn, N.Y.

[73] Assignee: John Morris Co., Inc., South Plainfield, N.J.

[21] Appl. No.: 319,402

[22] Filed: Mar. 3, 1989

Related U.S. Application Data

[63] Continuation-in-part of Ser. No. 223,167, Jul. 22, 1988, abandoned.

[51] Int. Cl.$^5$ .................... A61K 37/12; A61K 35/14; A61K 35/16
[52] U.S. Cl. .................................. 424/543; 424/529; 424/530; 514/2; 514/21; 514/842; 514/859; 514/861; 514/863; 514/886; 514/887
[58] Field of Search ................. 424/543, 529, 530, 10, 424/11, DIG. 4, 616; 514/21, 842, 859, 861, 863, 886, 887

[56] References Cited

U.S. PATENT DOCUMENTS

| | | | |
|---|---|---|---|
| 2,413,983 | 1/1947 | Lustig et al. | 530/357 |
| 2,434,688 | 1/1948 | Evans | 264/202 |
| 2,474,339 | 6/1949 | Ward et al. | 252/315.1 |
| 2,540,494 | 2/1951 | Schwarz | 132/905 |
| 2,631,965 | 5/1950 | Schnell | 424/72 |
| 2,719,814 | 10/1955 | Haefele | 167/87.1 |
| 3,514,515 | 5/1970 | Woolf | 514/557 |
| 3,683,939 | 8/1972 | Johnsen et al. | 132/203 |
| 3,837,349 | 9/1974 | Jedzinak et al. | 132/207 |
| 3,842,848 | 10/1974 | Karjala | 132/204 |
| 3,954,974 | 5/1976 | Herzog et al. | 424/616 |
| 3,957,065 | 5/1976 | Busch et al. | 132/204 |
| 3,961,634 | 6/1976 | Busch | 132/208 |
| 4,158,704 | 6/1979 | Baer et al. | 424/72 |
| 4,195,095 | 3/1980 | Sheffner | 514/557 |
| 4,390,525 | 6/1983 | Yoshioka et al. | 424/71 |
| 4,426,376 | 1/1984 | Shirakura et al. | 424/71 |
| 4,427,651 | 1/1984 | Stroetmann | 424/46 |
| 4,438,102 | 3/1984 | Ganci | 424/616 |
| 4,450,097 | 5/1984 | Nakatani et al. | 252/404 |
| 4,459,284 | 7/1984 | Azuma et al. | 424/72 |
| 4,530,828 | 7/1985 | Smith et al. | 424/61 |
| 4,600,028 | 7/1986 | Edman et al. | 132/221 |
| 4,605,555 | 8/1986 | Sato et al. | 424/85.4 |
| 4,711,780 | 12/1987 | Fahim | 424/641 |
| 4,818,520 | 4/1989 | Fleischner | 424/61 |

FOREIGN PATENT DOCUMENTS

| | | |
|---|---|---|
| 2522657 | 9/1983 | France. |
| 57-16810 | 1/1982 | Japan. |
| 2160419 | 4/1980 | United Kingdom. |

OTHER PUBLICATIONS

"Activated Conditions'" Based on Kerasol and Croquat WKP—private communication from supplier—may be published.
*Veterinary Pathology*, 4th Edition, Smithy, Jones and Hunt; Editors (Lee & Feberge, Philadelphia, 1972) pp. 1037–1038.
*Atlas of Skin Diseases of the Horse; Diagnosis and Treatment in Equine Dermatology*, Montes and Vaughan, Editors, 1983 by W. B. Saunders, pp. 38, 150, 178, 184.
Puri, A. K. and R. T. Jones, An Approach to Permanent Hair Conditioning, Preprints of the XIVth I.F.S.C.C. Congress, Barcelona, 1986 vol. II.
Neurath, The Proteins, vol. IV, Academic Press, New York, 1966, pp. 318–319.
"The Chemistry of Proteins", from *Biochemistry*, Ed. Cranslow & Shepratz, 1967, Chapter 3, p. 59.
*Science and Technology of Gelatin*, Ed. Ward & Courts (Academic Press), pp. 78, 81, 85 and 101–107.
*The Chemistry and Manufacture of Cosmetics*, Ed. M. G. DeNavarre, vol. IV, 2nd Ed., 1975, Chapters 5, 21, 59.
C. P. McCord, "The Physiologic Properties of Thioglycolic Acid and Thioglycolates", *Industrial Medicine*, (Dec., 1946) pp. 669–676.
A. K. Puri, International Journal of Cosmetic Science, 1, 59, 1979.
L. L. Gershbein, Journal of Pharmaceutical Sciences, 68, 1230, 1989.
D. M. Stuart "Blood Coagulants and Anticoagulants", S. D. Gershon and M. M. Rieger "Thioglycolic Acid", S. D. Turk "Thiols" all in *Kirk–Othmer's Encyclopedia of Chemical Technology*, Second Edition.

*Primary Examiner*—Douglas W. Robinson
*Assistant Examiner*—Jean C. Witz
*Attorney, Agent, or Firm*—Henry D. Coleman; R. Neil Sudol

[57] ABSTRACT

This invention relates to activated protein-containing compositions comprising reducing agents, oxidizing agents and/or anti-oxidants and methods of use. The therapeutic compositions and methods of the present invention are particularly effective in promoting wound healing, and in inhibiting certain skin disorders, including eczema and seborrhea, sclerodema and acne. The therapeutic compositions and methods of the present invention have also shown enhanced effect as veterinary tools in reducing the debilitation associated with certain skin conditions in mammals including eczematoid dermatitis, chronic dermatitis, equine exuberant granuloma ("proud flesh"), decubitis ulcers, and canine cutaneous granulomas ("lick" granuloma).

34 Claims, No Drawings

COMPOSITIONS AND METHODS FOR TREATING SKIN CONDITIONS AND PROMOTING WOUND HEALING

BACKGROUND OF THE INVENTION

This is a continuation-in-part application of U.S. patent application Ser. No 223,167, entitled "Method for Treating Skin Conditions Utilizing Novel Pharmaceutical Compositions", filed July 22, 1988, now abandoned.

This invention relates to therapeutic compositions using novel activated protein-containing ingredients and includes reducing agents and optionally, oxidizing agents and/or anti-oxidants. The therapeutic compositions of the present invention are particularly effective in promoting wound healing, and in inhibiting certain skin disorders, including eczema and seborrhea, dandruff, psoriases and other rash-like indications, scleroderma and acne. The therapeutic methods of the present invention have also shown enhanced effect as veterinary tools in reducing the debilitation associated with certain skin conditions in mammals including eczematoid dermatitis, chronic dermatitis, equine exuberant granuloma ("proud flesh"), decubitis ulcers, and canine cutaneous granulomas ("lick" granuloma).

U.S. Pat. No. 4,438,102 describes compositions which are useful for promoting the growth of normal dermal and epidermal tissue, and described as being useful to promote wound healing in the soft keratin tissue of the epidermis. The compositions of the patent are described as containing defined percentages of thioglycollic acid, ammonium hydroxide, glycerine, citric acid, hydrogen peroxide, gelatin, a lower alkanol, and a solvent such as acetone or diethyl ether. Several examples of wound healing are provided in the specification. The commercial gelatins described in the patent do not contain sufficient cysteinyl residues to covalently bind to keratinous tissue, especially skin and the patent does not disclose that the gelatin covalently binds to skin.

U.S. Pat. No. 3,954,974 describes disinfectant emulsions comprised of hydrogen peroxide in an oil-in-water phase. Exemplary compositions comprise hydrogen peroxide, an emulsifier or surfactant, an oil or gel and water. Certain embodiments may additionally include solvents. The compositions of the patent may be used for disinfecting hands and for treating skin diseases, irritations and injuries.

U.S. Pat. No. 4,195,095 describes the use of certain formulations comprising thioglycollic acid for use in the treatment of fatty cysts, dandruff, scleroderma and other dermatological disorders, including acne vulgaris. Exemplary compositions comprise thioglycollic acid, hexachlorophene, sodium hydroxide, water and other ingredients, including bulking or gelling polymers and preservatives, among others.

It has now been discovered that activated protein compositions which are formulated with reducing agents, and with or without oxidizing agents and/or anti-oxidant compositions exhibit surprising activity for treating wounds, pyoderma, sebborhea, psoriasis, acne, itching, callouses, corns, burns, eczematoid dermatitis, chronic dermatitis, decubitis ulcers, miscellaneous rashes, non-specific dermatitis and certain veterinary conditions including equine exuberant granuloma ("proud flesh") and canine cutaneous granulomas ("lick" granuloma). Especially advantageous characteristics of these compounds include storage stability and the ability to effectuate a reduction and oxidation process to form covalent disulfide linkages without having to resort to two separate solutions. Thus, the essential ingredients of the compositions of this invention are the reducing agent and the activated protein, and optionally an oxidizing agent and/or an antioxidant may be added. Numerous additional components may also be included, for example water, bases, acids, buffering agents, emulsifying agents or surfactants, thickeners, preservatives, coloring agents and perfuming agents.

It is an object of the present invention to provide novel therapeutic compositions and methods for treating certain skin conditions for example, wounds, eczematoid dermatitis, chronic dermatitis, decubitis ulcers, sebborhea, psoriasis, pyoderma, dandruff, itching, allergic skin reactions, miscellaneous rashes, acne and certain veterinary conditions including equine exuberant granuloma, and canine cutaneous granulomas ("lick" granuloma) utilizing compositions containing at least one activated thiol-containing protein in combination with a reducing agent.

It is a further object of the present invention to provide therapeutic compositions and methods for treating the aboveidentified skin conditions with storage stable compositions which are capable of maintaining the activity of an activated protein in the presence of an oxidizing agent to promote the shelf-life of the composition.

It is a further object of the present invention to provide compositions for treating chronic veterinary skin conditions which do not respond to traditional therapeutic methods, for example, equine exuberant granuloma ("proud flesh") and canine cutaneous granuloma ("lick" granuloma).

It is an additional object of the present invention to provide new compositions and methods for conditioning keratinous tissue including skin, by exposing the tissue to activated protein and reducing agent and oxidizing said tissue without having to apply two separate solutions to the treated tissue to perform the reducing and oxidizing steps. This approach has shown surprising efficacy in treating the above-mentioned skin conditions.

BRIEF DESCRIPTION OF THE INVENTION

The thereapeutic compositions and methods of the present invention are useful for treating certain skin conditions for example, wounds, sebborhea, psoriasis, dandruff, allergic skin reactions, acne, itching, callouses, corns, burns, miscellaneous rashes, non-specific dermatitis and certain veterinary conditions including eczematoid dermatitis, chronic dermatitis, equine exuberant granuloma ("proud flesh"), decubitis ulcers, and canine cutaneous granuloma ("lick" granuloma). In using the present invention a composition comprising an activated protein, a compatible reducing agent, and optionally an oxidizing agent and/or an antioxidant is contacted with an area of keratinous tissue affected with one of the above conditions. The therapeutic compositions and methods of the present invention have shown especially surprising activity against non-healing skin conditions, especially canine cutaneous granulomas ("lick" granuloma) and equine exuberant granuloma ("proud flesh").

Compositions useful in the therapeutic methods of the present invention include aqueous compositions having a pH of from about 4.0 to about 9, preferably a pH of about 7 to about 8, and most preferably a pH of about 7.6 (physiological pH). Compositions of the present invention may comprise a reducing agent, and an activated protein, in addition to other less essential components, and optionally an oxidizing agent and/or an antioxidant. Additional embodiments of the present invention may comprise a reducing agent, an activated protein, and an antioxidant. The compositions containing an antioxidant may also contain an oxidizing agent. In those compositions where an antioxidant is used in combination with an oxidizing agent, it is preferred that the antioxidant used is a volatile antioxidant and the oxidizing agent used is a non-volatile oxidizing agent.

The protein used is an activated protein. An activated protein is a protein which has been subjected to a reducing agent, for example a thiol-containing compound, which results in the breaking of disulfide bonds of cystine residues within the protein structure to produce free thiol or mercaptide groups on cysteine residues. The ability of a protein to bind to keratinous tissue is believed to be related in part to the number of thiol or mercaptide groups on the protein which are free to bind to mercaptide or thiol groups on the keratinous tissue. Also, it is believed that the ability to oxidize the keratin mercaptide and a proximal protein mercaptide aids the formation of disulfide covalent bonds. Any promotion in growth related to the binding of protein to keratinous tissue would be expected to be of greatest duration where covalent bonding as opposed to electrostatic or ionic binding occurs.

It is preferred that the activated protein should be hydrated. A hydrated protein may be beneficial to certain types of skin conditions and wounds, especially burns, because the hydrated protein may be expected to provide additional moisture to the skin. The protein in the compositions of the present invention may react with and form chemical bonds with the keratin of human and animal skin, thus effecting an attachment of moist hydrated proteins to skin. The compositions are therefore useful for treating human and animal skin to chemically bond the activated protein to the skin, moisturize dry skin and provide a moisturizing vehicle to carry other agents into dehydrated skin.

The percent of activated protein that bonds to the keratinous tissue will vary with the concentration of reducing agents in the composition and the number of activated thiol or mercapto groups in the activated protein and the keratinous tissue. The time that the reducing agent is in contact with the keratinous tissue is also important; the longer the keratinous tissue is in contact with the reducing agent, the greater will be likelihood of protein-keratinous tissue covalent bond formation.

The therapeutic compositions of the present invention are preferably utilized at ambient temperatures, i.e., about 20° C. to about 35° C.; however, higher temperatures may be used. Obviously, when treating a wound, especially a burn, treatment is kept to a lower temperature to avoid exacerbating the wound condition. Where the application of heat is viewed as therapeutic, conducting the treatment at higher temperatures is recommended. The keratinous tissue may be treated over a period of time ranging from about 10 minutes to about 6 hours. The keratinous tissue may be treated acutely or chronically, with or without a dressing as needed. In certain embodiments, compositions useful in practicing the therapeutic methods of the present invention may be formulated with sustained or controlled release polymers to produce formulations capable of delivering active agent for extended periods of time. Reaction is effected by bringing the compositions of the present invention into contact with the keratinous substrate to be treated and allowing the treated tissue to dry. The time of contact may be varied at will.

Depending upon the anti-oxidant used the reaction may be facilitated by heat. By removing the antioxidant in this way, oxidation to promote covalent disulfide formation by the oxygen in ambient air may be promoted. Preferred compositions may employ non-volatile oxidizing agents which may promote oxidation after the volatile antioxidants are removed from the formulations.

In one aspect of the present invention, compositions of the present invention comprise about 0.01 to about 12.0% by weight of an activated protein component, about 0.1 to about 15% by weight of a compatible reducing agent, about 0.001 to about 4.0% by weight of an oxidizing agent, and at least one component selected from the group consisting of water, acids, bases, buffering agents, emulsifying agents or surfactants, thickeners, preservatives, organic solvents, coloring agents and perfuming agents.

Compositions for use in the therapeutic method of the present invention may include an antioxidant instead of an oxidizing agent, and in certain embodiments no oxidizing agent or antioxidant is used. Exemplary compositions comprise about 0.01 to about 12.0% by weight of an activated protein component, about 0.1 to about 15% by weight of a compatible reducing agent, at least one component selected from the group consisting of water, acids, bases, buffering agents, emulsifying agents or surfactants, thickeners, preservatives, organic solvents, coloring agents, preservatives and perfume agents, and optionally about 0.001 to about 4.0% of an antioxidant and/or an oxidizing agent.

Additional embodiments of the method of the present invention utilize a composition comprising about 0.01% to about 12.0% by weight of an activated protein component, about 0.1 to about 15% of a compatible reducing agent, about 0.001 to about 4.0% by weight of an oxidizing agent and about 0.01 to about 4.0% by weight of antioxidant, preferably a volatile antioxidant and at least one component selected from the group consisting of water, acids, bases, buffering agents, solvents, emulsifying agents or surfactants, thickeners, coloring agents, preservatives and perfume agents.

The compositions utilized in the methods of the present invention are formulated to enhance the formation of free mercaptide or thiol groups in the protein and the keratinous tissue to maximize the probability that a free thiol in the protein and a free thiol in the keratinous tissue will interact to form a covalent disulfide bond. The inclusion of an oxidizing agent in the same composition as the reducing agent and activated protein is designed to maximize covalent disulfide formation without having to resort to a second oxidizing solution.

In addition to covalent disulfide bond formation, a number of other mechanisms may be responsible for the enhanced activity displayed by the therapeutic methods of the present invention.

The present invention utilizes compositions formulated as gels, creams, lotions, sprays or liquids of varying viscosities.

DETAILED DESCRIPTION OF THE INVENTION

The present invention employs compositions comprising an activated protein, a compatible reducing agent, optionally an oxidizing agent and/or an antioxidant, and at least one component selected from the group consisting of water, bases, acids, buffering agents, emulsifying agents or surfactants, thickeners, preservatives, organic solvents, coloring agents and perfuming agents.

In these compositions, the activated protein comprises about 0.01 to about 12% by weight of the composition, preferably about 1.0 to about 5.0% by weight for certain formulations and about 6 to 10% by weight for other applications where more concentrated formulations are found to be advantageous.

Activated proteins used in compositions employed in the present invention are exemplified by keratins or certain types of gelatins containing sufficient cysteinyl content, i.e., at least about 1 cysteine amino acid for every 200 amino acids in a peptide chain (approximately, at least about 0.5% by weight cysteine, preferably, at least about 1.0% by weight cysteine, and most preferably at least about 5% by weight cysteine) to covalently bind to the keratinous tissue of hair, skin and nails to produce a durable permanent bond to keratinous tissue. By permanent bond we mean that the protein is not easily washed or rubbed off from the keratinous tissue and becomes as permanent as normal hair and nails. A large number of exemplary proteins may be used in the present invention and include keratin, food proteins, for example, casein, alpha and beta-lactalbumin, seed proteins, for example, soybean proteins, linseed protein, cotton seed protein, corn protein and peanut protein, among others, hemoglobin, insulin, myosin, zein, ovalbumin, hemoglobin, trypsin, chymotrypsin, chymotrypsinogen, elastases, thrombins, plasminogen, fibrinogen/fibrin, lysozyme, papain, human serum albumin, heat coagulable mucoproteins isolated from cartilage, bones and skin, gamma globulin blood proteins, and a number of the blood factor proteins, including, for example, factor VIII, XII, IXa and Xa, among others. Of course, proteins which contain large numbers of cysteinyl residues are preferred, because these proteins would form the greatest number of covalent bonds with the keratinous tissue and thus, produce the greatest durability. It is to be noted that the commercial gelatins disclosed in U.S. Pat. No. 4,438,102 contain at most trace cysteinyl residues and most commercial grade gelatins, including Grade A edible gelatin, contain undetectable amounts of cysteine. Such gelatin proteins, which do not contain sufficient cysteinyl content to covalently bind to keratinous tissue in any significant way, i.e., to produce a permanent attachment of the protein to the keratinous tissue, are therefore not contemplated for use in the present invention.

Preferred proteins for use in the present invention include proteins containing high percentages by weight of cysteine, for example, ribonuclease T1, human serum albumin and gamma globulins. An especially preferred protein for use in the present invention is keratin, because of its particularly high cysteine content (about 12% to about 17% by weight of cysteine). In compositions to be used to treat certain wounds, exemplary compositions utilize keratin either alone or in combination with fibrinogen/fibrin or modified fibrinogen. Other compositions which may be used to treat wounds may comprise fibrinogen/fibrin or modified fibrinogen alone.

The proteins used in the present invention are preferably activated in the presence of reducing agent at a pH of about 9.0 or above for a time sufficient to produce free thiol group. This period is generally about 5 minutes up to about one hour. Activation periods of greater than one hour are less preferred because although such activation periods may marginally increase the amount of activated thiol groups in the protein, such periods also result in hydrolysis of the protein into shorter, less advantageous peptide units. A number of globular proteins contain cysteinyl residues within hydrophobic pockets. To activate these proteins and expose cysteinyl groups which exist in hydrophobic pockets to the keratinous tissue, it may be necessary to subject the proteins to denaturation and activation so that an activated cysteinyl residue of the denatured protein may be placed in proximity to the cysteinyl residues of the keratinous tissue to promote covalent binding.

The proteins of the present invention are preferably activated in the presence of reducing agent separately before they are formulated with the other components, because the addition of components other than a reducing agent at a pH above about 9.0 may adversely may adversely affect the rate at which cystinyl disulfide bonds in the protein are converted to cysteinyl mercaptide groups. This may lower the overall activity of the protein. However, although less preferred, it is possible to generate activated protein after formulation by simply exposing unactivated protein to reducing agents during storage below pH 7.0, provided that the cysteinyl content of the protein is sufficiently high to activate enough cysteinyl residues to promote covalent binding to the keratinous tissue.

The activated protein is preferably a keratin, but any protein which contains sufficient cysteinyl content to promote binding to activated keratinous tissue is contemplated for use in the present invention. Preferred proteins are keratins because of their high cysteinyl content (generally, greater than 10% by weight of the protein and often as high as 15–17% by weight of the protein) which may be obtained by hydrolysis of skin, feathers, wool and hair. A particularly preferred keratin is Kerasol TM from Croda Chemicals International, Chesire, England. The molecular weight of proteins useful in the present invention preferably varies between about 5,000 and 500,000 Daltons, and most preferably varies between about 120,000 and 130,000 Daltons.

Reducing agents which are useful to activate protein in the present invention include sulfides, thiol-containing compositions including dithiothreitol, trithiohexitol, glutathione, cysteine, mercaptoethanol, thioglycerol, thioalkanoic acid and mercaptocarboxylic acid analogues, for example, mercaptosuccinic acid, thiolactic acid and their pharmaceutically acceptable salts, among others, among others, including thioglycollic acid and salts of thioglycollic acid. Preferred reducing agents for activating the protein are thioglycerol, cysteine, thiolactic acid and thioglycollic acid, and their pharmaceutically acceptable salts. Especially preferred reducing agents for use in the present invention include thioglycerol and salts of thioglycollic acid, especially ammonium thioglycollate. It is preferred that the reducing agent for activating the protein should be the same as the pharmaceutically compatible reducing agent which is used in the final formulation of the invention. The use of strong pharmaceutically incompatible reducing agents to activate the protein are less preferred and may make the use of the protein more difficult because the reducing agent may have to be removed from the activated protein before formulation.

Compositions for use in the method of the present invention also contain a pharmaceutically compatible reducing agent in an amount equal to about o.1 to about 15% by weight of the formulation. Preferred compositions contain about 3.0 to about 10% by weight of a pharmaceutically compatible reducing agent. The amount of pharmaceutically compatible reducing agent varies according to the therapeutic use for which the compositions are intended, but generally falls within the range of about 3.0 to about 10% by weight. A pharmaceutically compatible reducing agent is an agent which reduces cystinyl disulfide linkages in keratinous tissue to produce free thiol or mercaptide groups and is compatible with biological and/or pharmaceutical systems, especially for use on the skin of humans and/or animals. Pharmaceutically compatible reducing agents which are contemplated for use in the present invention include mercaptoethanol, dithiothreitol, thioglycerol, thiolactic acid, glutathione, cysteine and thioglycollic acid and its salts. An especially preferred reducing agent is ammonium thioglycollate.

Compositions used in the present invention may additionally comprise about 0.001 to about 4.0% by weight of an oxidizing agent. Preferred embodiments comprise about 0.1 to about 1.0% of the oxidizing agent and most preferably comprise about 0.5% to about 1.0% of the oxidizing agent. The oxidizing agent is included in compositions of the present invention to enhance oxidation and also to promote the formation of covalent disulfide bonds between activated protein and keratinous tissue. Additionally, the oxidizing agent may function as a disinfecting agent to clean the keratinous tissue and enhance healing. Exemplary oxidizing agents include hydrogen peroxide (which may or may not be stabilized with, for example, urea) and its salts including ammonium sulfate peroxide, urea peroxide, pyrophosphate peroxide, carbonate peroxide, organic peroxides including acetyl peroxide, benzoyl peroxide, among others, alkali metal perborates including sodium perborate, the alkali metal bromates including sodium and potassium bromate and sodium and potassium iodate. In embodiments of the present invention which do not include an antioxidant, hydrogen peroxide is the preferred oxidizing agent. In the embodiments which include hydrogen peroxide, it is preferred that the amount of hydrogen peroxide should be in an amount equal to about 0.001 to about 1.5% by weight of the composition and most preferably about 0.05 to about 1.0%. Where oxidizing agents other than hydrogen peroxide are used, a higher percentage by weight is usually used compared to hydrogen peroxide which has a high oxidation equivalent per unit weight.

Of course, many of the therapeutic compositions and methods, especially those which are used to treat the veterinary conditions of equine exuberant granuloma ("proud flesh") and canine cutaneous granuloma ("lick" granuloma) do not require the inclusion of an oxidizing agent, but it is often advantageous to include the oxidizing agent. Thus, where oxidizing agent is not included to treat keratinous tissue conditions, the compositions comprise no greater than about 12.0% of an activated protein component and no greater than about 15.0% of a reducing component, the remainder of the composition comprising at least one component selected from the group consisting of water, bases, acids, buffering agents, emulsifying agents or surfactants, thickeners, preservatives, organic solvents, coloring agents and perfuming agents.

In addition to the above-described ingredients, additional components may be added to the formulation to enhance the effects of the compositions. In addition to water, additional components may include bases, acids, buffering agents, solvents, emulsifying agents or surfactants, thickeners, preservatives, organic solvents, coloring agents and perfuming agents.

Exemplary acids and bases are added to adjust the pH of the formulation to desired levels. Preferred acids include organic acids for example acetic acid, citric acid and tartaric acid, among others, and inorganic phosphoric acid including its salts such as the salts of mono- and di- hydrogen phosphoric acid. The inorganic phosphoric acid salts may also be included in the formulations as buffering agents. Preferred bases include organic amines, for example, monoethanolamine, triethanolamine, trimethylamine and triethylamine. Most preferred bases include ammonium hydroxide.

Buffering agents, for example the inorganic phosphoric acid salts indicated above, as well as other buffering agents, for example the salts of organic acids such as acetic acid and citric acid may be included in the formulations of the present invention in amounts effective to maintain the pH of the formulation over time. Preferably, the amount of buffering agent is no more than about 1.5% by weight of the formulation and most preferably is less than 0.75% by weight. The pH of the formulation may be a factor in determining its stability and in maintaining the activity of certain components in the formulation, especially the activated protein and the compatible reducing agent. Thus, a buffering agent may be included within the formulation to maintain the pH at a relatively constant level over time.

To add homogeneity to and promote the solubility of the formulation, certain organic solvents may be included. Among the solvents that may be useful in certain embodiments of the present formulation include water soluble polar organic solvents for example alkanols such as methanol, ethanol, propanol, butanol and carbonyl containing solvents for example acetone, butanone and the like, among others. Additional solvents include ethers and amines, for example diethyl or dipropyl ether and trimethyl or triethyl amine. Trimethylamine and triethylamine may also be added as bases.

The solvent added to the formulation may enhance the solubility of certain components. Where liquid formulations are contemplated, it is sometimes advisable to add an organic solvent to promote the solubility of certain less polar components, which without the added organic solvent may be only marginally soluble in water resulting in formulations having more than one phase. The addition of the organic solvent may produce a uniform, homogeneous single phase.

Emollients may also be included, especially in lotions to produce a uniform, homogeneous single phase and provide other favorable characteristics. An especially preferred emollient for use in formulations of the present invention is PPG 15-sterol ether which also may be added to the formulations of the present invention for its emulsifying characteristics.

An emulsifying agent or surfactant is often added to embodiments of the present invention to enhance the characteristics of the formulation, to promote the solubility of the protein and other components and the phase stability of the formulation. Such agents also provide detergent-like qualities to the formulations. Suitable surfactants or emulsifying agents may be non-ionic, anionic or amphoteric. Nonionic emulsifying compositions products of hydrophobic compounds, for example ethylene oxide condensation products with higher fatty acids, higher fatty alcohols or alkylated aromatic hydrocarbons, higher molecular weight polypropylene glycols, amide and amine condensation products of which N-bis (2-hydroxyethyl)-lauramide is exemplary. Preferred nonionic emulsifying compositions include polyoxyethylene ethers including polyoxyethyleneisohexadecyl ether, for example Arlasolve 200 TM (available from ICI Americas, Wilmington Del.), polyoxyethylenelauryl ether, for example Brij 35 TM (ICI), polyoxyethylenestearyl ether, for example Brij 72 TM, and Brij 78 TM (ICI) and polyoxypropylenestearyl ether, for example PPG-15 stearyl ether (Arlamol E, ICI). Other exemplary emulsifiers include ethoxylated lanolin, for example, Lanogel 41 (Amerchol, Inc., Edison, N.J.). Exemplary anionic surfactants include sulfuric acid esters of polyhydric alcohols, e.g. lauryl sulfate, cetyl sulfate, etc., higher fatty alcohol sulfates derived from coconut oil, hydroxy sulfonated higher fatty acid esters such as, e.g., higher fatty acid esters of 2,3-dihydroxypropane sulfonic acid, higher fatty acid esters of low molecular weight alkylol sulfonic acids, e.g., oleic acid ester of isethionic acid, sulfated higher fatty acid alkylolamides such as e.g., ethanolamide sulfates, higher fatty acid amides of amine alkyl sulfonic acids, e.g., lauric amide of taurine, among others, and aromatic containing anionic synthetic surfactants. Exemplary amphoteric surfactants include the salts of N-alkyl compounds of betaamino propionic acid wherein the alkyl group is derived from a fatty acid such as a mixture of cocoanut oil fatty acids, among others.

It may be preferable to add an anti-foaming agent to certain compositions to promote homogeneity and prevent foaming from surfactant action. A preferred anti-foaming agent for use in embodiments of the present invention includes, for example, Dimethicone TM, available from Dow Chemical Corp., Midland, Mich.

Thickeners or gelling agents may be added to provide additional weight and a more viscous feel to the formulations. Suitable thickening agents include polyvinyl pyrollidone, for example PVP K30 (GAF Charllotte, N.C.) polyacrylates, carbomers, for example carboxyvinyl polymer such as Carbapol 940 (available from B. F. Goodrich, Cleveland, Ohio) polyoxyethylene stearyl ethers, for example, polyoxyethylene-2 stearyl ether such as Steareth 2 TM (ICI) and polyoxyethylene-20 stearyl ether such as Steareth 20 TM (ICI), sodium alginate, carageenan, agar, ethoxylated polyvinyl alcohol, gums, for example methylcellulose, hydroxymethylcellulose, carboxymethylcellulose, propylcellulose and hydroxypropylcellulose, acacia, tragacanth, guar, and quince, among others. In compositions which are contemplated to be formulated as a gel or lotion, Isoseteth 20 TM (polyoxyethyleneisohexadecyl ether, ICI), and Steareth 2 TM and 20 TM are preferred for use as thickening agents. In compositions which are contemplated to be formulated as creams, preferred thickeners include Steareth 2 TM and Steareth 20 TM and the carbomer polymers, for example Carbapol 940 TM.

Preservatives are added for preventing microbial growth in the presence of protein nutrients. Exemplary preservatives include benzoic acid analogs including, among others, sodium benzoate. Other presevatives include propyl and methyl paraben, Dowicil TM (Dow Chemical Corp., Midland, Mi.) and formaldehyde solution. An especially preferred preservative is Germaben II TM, available from Sutton Laboratories, N.J.

Coloring agents and perfume agents may also be added to enhance the characteristics of the formulations.

In another aspect of the present invention, the compositions include an antioxidant instead of an oxidizing agent. These compositions comprise about 0.01 to about 12% by weight of an activated protein component, about 0.1 to about 15% by weight of a compatible reducing agent, about 0.001 to about 2.0% by weight of an antioxidant, and at least one component selected from the group consisting of water, acids, bases, buffering agents, emulsifying agents or surfactants, thickeners, coloring agents and perfume agents.

In compositions comprising an antioxidant, the antioxidant is included to promote the storage stability of the formulations. Exemplary antioxidants may include alphatocopherol, hydroxyquinone, unipherol, tocopherol ascorbate, lecithin, chlorophyll, ascorbylpalmitate, linseed oil, tongue oil, other natural antioxidants such as the steam distillation extract of rosemary as disclosed in U.S. Pat. No. 4,450,097, thiazoline carboxylate, dihydroquinolines, methyl gallate, propyl gallate, alkylaryl and diarylamines.

Certain chelating agents, for example, EDTA, may be employed to enhance the antioxidant effect of the above agents. The chelating agent may function to chelate any dissolved metals which may be responsible for the in situ generation of oxygen. Preferably, the chelating agent comprises between about 0.001 to about 0.5% of the formulation and most preferably comprises no more than about 0.1% of the formulation.

Preferably, in compositions which employ an antioxidant, a volatile antioxidant is used. Volatile antioxidants provide the advantage of protecting the activated protein and reducing agent from oxidation during storage. In addition, because the antioxidants are volatile, after the compositions are placed on the treatment area and exposed to air or a heat source, the antioxidant will evaporate from the treatment area leaving the remaining protein and activated keratinous tissue to be air oxidized. Volatile antioxidants include voltile carbonyl containing compounds, hindered phenolic compounds, for example 2,4,6-trialkyl phenols, butylated hydroxyanisole (BHA), butylated hydroxytoluene (BHT), p-hydroxyanisole and p-hydroxytoluene.

A volatile antioxidant as used in preferred embodiments of the present invention is an antioxidant that volatilizes or evaporates from the treatment area under normal drying conditions. Non-volatile antioxidants, although useful in certain aspects of the present invention, are less preferred than are volatile antioxidants, which are added to formulations for their ability to stabilize the active ingredients over time while in storage and their ability to be removed from the treatment area under normal drying conditions. Preferred volatile antioxidants include those that are more easily volatilized, i.e., will evaporate more quickly from the treatment surface.

Certain antioxidants may be formulated in combination with solvents including water. Formulations including solvents may promote solvent/antioxidant azeotrope formation and volatility of the antioxidant. Azeotrope formation with water or with other solvents may result in the antioxidant volatilizing at a temperature lower than normal. Thus, by formulating the compositions with, for example, an alcoholic or other solvent, the volatilization of the antioxidant may be enhanced, resulting in an enhanced rate of oxidation of the treated keratinous tissue. Where solvents are used, it is preferred that a pharmaceutically compatible solvent is used.

In preferred embodiments of the present invention, when an oxidizing agent is not included in the formulations utilized, about 0.01% to about 2.0% of antioxidant is included in the formulations. Without the additional oxidizing agent, the antioxidant is included to prevent atmospheric oxygen or oxygen dissolved in the solution from deactivating the protein during storage. In compositions in which oxidizing agents are employed to promote the oxidation of free thiols or mercaptides to covalent disulfide bonds, the oxidizing agent comprises about 0.001% to about 4.0% by weight of an oxidizing agent and the antioxidant comprises about 0.01% to about 4.0% of the formulation.

In formulations useful in the present invention comprising an antioxidant or an antioxidant and oxidizing agent, the formulations may additionally comprise acids, bases, buffering agents, emulsifying agents or surfactants, thickeners, preservatives, organic solvents, coloring agents and perfume agents as described for other embodiments of the present invention. In formulations comprising an antioxidant, a volatile antioxidant is preferred. In such formulations, additional organic solvent may be added to promote the volatilization of the antioxidant. It is recognized that the choice of additives is made to avoid any interactions that may affect the activity of the activated protein, reducing agent, oxidizing agent or antioxidant.

Compositions of the present invention may be used to treat acne. Preferred compositions for treating acne include the compositions of the present invention in combination with pharmaceutically effective amounts of benzoyl peroxide, tetracycline and other anti-acne agents. The compositions of the present invention may also be used to resolve pock marks and acne scars in individuals who have not had acne for years.

Compositions of the present invention may also be used to treat dandruff. Especially preferred compositions for treating dandruff include the compositions of the present invention in combination with an effective amount of a traditional anti-dandruff agent, for example, zinc pyrithione.

The compositions useful in present invention are applied to the treatment area as a liquid, cream, gel or lotion by rubbing the compositions into the keratinous tissue to be treated. Following application, the compounds are allowed to dry. This may be accelerated by the use of heat or circulating air. Subsequent to drying, formulations may be washed off all together, although this is not preferred when the compositions are used to treat wounds. When treating dandruff or sebborhea, the compositions may be washed off before drying.

The methods of the present invention comprise exposing the area of keratinous tissue to be treated to any one of the compositions previously described hereinabove. Depending on the type of skin condition to be treated, the therapeutic compositions are applied to the affected area at least once a day and as many times a day as are necessary to produce an improved condition. Generally, the therapeutic compositions are applied to the effected area between one and four times a day. Applications of fewer than once a day may be performed depending upon the indication and severity. For example, in the treatment of dandruff, sebborhea and skin conditions other than wounds, the formulation need only be applied after or during shampooing, which may only be once or twice a week. The duration of therapy will depend on the condition treated and on the response of the condition to the thereapy. Thus, when chronic conditions that do no respond to traditional therapy are being treated, it is to be expected that the duration of therapy will be longer than when less severe conditions are treated.

Although the present invention is not bound by theory, it is believed that the surprising therapeutic activity exhibited by compositions useful in the present invention may be the result of a combination of pharmacological effects. It is believed that the activity of these compositions may be the result of the combined effects of many possible mechanisms of action, including; moisturization of the affected area by hydrated protein, film formation, cytoskeletal interaction and mediation of the clotting process, disulfide covalent bond formation, the release of endogenous mediators including fibronectin, receptor modification and vasodilation.

The following examples are provided to illustrate the present invention and should not be construed to limit the scope of the invention of the present application in any way.

EXAMPLE 1 Dilute Liquid

| Component | Weight Percent | |
|---|---|---|
| Ammonium Thioglycollate pH 9 | 3.27 | A |
| Kerasol | 0.95 | |
| Propylene Glycol | 0.05 | B |
| Lanogel 41 | 0.05 | |
| Brij 35 | 0.13 | |
| PVP-K30-25% Sol. | 0.22 | |
| Glycerine | 0.16 | C |
| Citric Sol (2%) | 0.04 | |
| Hyd. Peroxide (3%) | 0.53 | |
| Acetone | 0.13 | |
| Isopropyl Alcohol 70% | 0.53 | |
| Kerasol | 1.90 | |
| Water - Distilled | 85.42 | D |
| Germaben II | 0.93 | E |
| Fragrance | 1.90 | F |
| Arlasolve | 3.79 | |

Procedure: Add a mixture of Components B to ½ of Component D at 100° F. and mix for 5 minutes in a high speed blender. After thoroughly mixed, add a mixture of Components C and mix for 5 minutes. Let the mixture cool and add the balance of component D to the mixture at room temperature and mix for 2 minutes. Prepare A by adding 9.64% of a 28% ammonia solution to 90.64% of a 60% ammonium thioglycollate water solution. pH should read 9; if not, add more ammonia solution. Add kerasol TM to ammonium thioglycollate solution and mix until well homogenized. Let stand for at least five minutes. This procedures mixture A. Add A to the BDC mixture and then mix in a high speed blender until thoroughly mixed. Next, add component E to mixture ABCD until thoroughly mixed. Finally add components F to mixture ABCDE and mix at high speed until homogeneous.

| EXAMPLE II Concentrated Liquid | | |
|---|---|---|
| Component | Weight Percent | |
| Ammmonium Thioglycollate pH 9 | 9.75 | A |
| Kerasol TM | 2.82 | |
| Propylene Glycol | 0.13 | B |
| Lanagel 41 TM | 0.13 | |
| Brij 35 TM | 0.39 | |
| PVP-K30 TM 25% | 0.64 | |
| Glycerine | 0.47 | C |
| Citric Acid Solution | 0.12 | |
| Hydrogen Peroxide (3%) | 1.55 | |
| Acetone | 0.39 | |
| Isopropyl Alcohol 70% | 1.68 | |
| Kerasol TM | 5.65 | |
| Water | 67.81 | D |
| Germaben II TM | 2.82 | E |
| Fragrance and Solubilizer (1:2) | 5.65 | F |

Procedure: Add a mixture of Components B to ½ of Component D at 100° F. and mix for 5 minutes in a high speed blender. After thoroughly mixed, add a mixture of Components C and mix for 5 minutes. Let mixture cool and add the balance of component D to the mixture at room temperature and mix for 2 minutes. Prepare A by adding 9.64% of a 28% ammonia solution to 90.64% of a 60% ammonium thioglycollate water solution. pH should read 9; if not, add more ammonia solution. Add kerasol TM to ammonium thioglycollate solution and mix until well homogenized. Let stand for at least five minutes. This produces mixture A. Add A to the BDC mixture and then mix in a high speed blender until thoroughly mixed. Next, add components E to mixture ABCD until thoroughly mixed. Finally add components F to mixture ABCDE and mix at high speed until homogeneous.

| Example III Lotion | | |
|---|---|---|
| Component | Weight Percent | |
| Example II Concentrated liquid | 32.19 | A |
| Non-Perfumed Moisturizing Lotion | 45.85 | B |
| Carbapol 940 - 2% Sol | 19.51 | C |
| Triethylamine | 1.225 | D |
| H₂O | 1.225 | |

Procedure: Add Component A to Component B (see below) and thoroughly mix. Then add Component C until a homogeneous mixture is made. Finally, adjust the pH of mixture ABC with the triethylamine/H₂O mixture to about 7.0.

| Non-Perfumed Moisturizing Lotion | | |
|---|---|---|
| Component | Weight Percent | |
| Arlamed E TM | 1.36 | A |
| Brij 72 TM | 5.23 | |
| Brij 78 TM | 1.32 | |
| Mineral Oil | 11.64 | |
| Propyl Paraben | 0.18 | |
| Water | 77.71 | B |
| Sodium EDTA | 0.09 | |
| Anti-Foam Dimethicone TM | 0.09 | |
| Methyl Paraben | 0.36 | |
| Propylene Glycol | 1.36 | |
| Dowicil 200 TM | 0.45 | C |
| Formaldehyde (37%) | 0.21 | D |

Procedure for Non-Perfumed Moisturizing Lotion Component: Add A to B at 160° F. mixing thoroughly. Mix and cool to 100° F. Add Components C and D, mixing thoroughly. Allow to cool to 80° F. Use at 80 F.

| EXAMPLE IV Thin Cream | | |
|---|---|---|
| Component | Weight Percent | |
| Non-perfumed Moisturizing Lotion | 8.70 | A |
| Carbopol 940 TM | 58.26 | |
| Triethanolamine | 2.61 | |
| Concentrated Liquid Example II | 28.70 | B |
| Fragrance | 1.74 | C |

Procedure: Mix components of A together and adjust pH with triethanolamine. Add Component B and thoroughly mix until homogeneous. Mix in fragrance until homogeneous.

| EXAMPLE V-THICK CREAM | | |
|---|---|---|
| Component | Weight Percent | |
| Example II Concentrated liquid | 30.22 | A |
| Concentrated Non-Perfumed Moisturizing Lotion | 9.16 | B |
| Carbapol 940 TM - 4% Sol | 58.50 | C |
| Fragrance | 2.14% | |

Procedure: Add Component A to component B (see below) and thoroughly mix. Then add Component C until a homogeneous mixture is made. Add Component D to produce a homogeneous thick cream.

| Concentrated Non-Perfumed Moisturizing Lotion | | |
|---|---|---|
| Component | Weight Percent | |
| Arlamol E TM | 2.33 | A |
| Brij 72 TM | 8.95 | |
| Brij 78 TM | 2.26 | |
| Mineral Oil | 19.94 | |
| Propyl Paraben | 0.31 | |
| Water | 63.15 | B |
| Sodium EDTA | 0.016 | |
| Anti-Foam Dimethicone TM | 0.016 | |
| Methyl Paraben | 0.7 | |
| Propylene Glycol | 2.33 | |

Procedure for Concentrated Non-Perfumed Moisturizing Lotion Component: Add A to B at 160° F. mixing thoroughly. Mix and cool to 80° F. Use at 80° F.

| EXAMPLE VI Concentrated Stock Solution | | |
|---|---|---|
| Component | Weight Percent | |
| Purified Water | 32.55 | A |
| Propylene Glycol | 0.14 | |
| Lanogel 41 | 0.14 | |
| Brij 35 | 0.40 | |
| Purified Water | 0.487 | B |
| PVP-K30 TM 25% | 0.163 | |
| Glycerine 99% | 0.48 | C |
| Citric Acid 5.88% Solution | 0.12 | |
| Hydrogen Peroxide (3%) | 1.55 | |
| Acetone | 0.40 | |
| Isopropyl Alcohol 99% | 0.91 | |
| Kerasol TM | 5.65 | |
| Water | 41.62 | D |
| Germaben II TM | 2.82 | |

| EXAMPLE VI Concentrated Stock Solution | | |
|---|---|---|
| Component | Weight Percent | |
| Ammonium pH 9.0 Thioglycollate (60%) | 8.81 | E |
| Ammonium Sol'n (28%) | 0.94% | |
| Kerasol TM | 2.82% | |

Procedure: Step 1: In a separate tank agitate B (water) very strongly and sprinkle B (PVP K-30) onto the Vortex. Mix until PVP K-30 solution is complete. Step 2: Charge a mixing tank with water at 35°-40° C. Add the A phase ingredient and mix thoroughly. Add the PVP K-30 solution and mix in well. Step 3: Mix C phase together in a plastic container. Warm to 35°-40° C. Add to step 2 and add the D phase. Step 4: In a plastic container, add ammonium thioglycollate and then ammonia solution slowly to bring the pH to 9.0. Add the Kerasol TM. Mix this solution well and add it to the batch.

| EXAMPLE VII | | |
|---|---|---|
| Component | Weight Percent | |
| Purified Water | 30.53 | A |
| PVP K-30 | 0.163 | |
| Lanogel 41 | 0.14 | |
| Propylene Glycol | 0.14 | |
| Brij 35 | 0.40 | |
| Essence of Pellitory | 0.50% | |
| Essence of Elder | 0.50% | |
| Glycerine | 0.48% | B |
| Citric Acid 5.88% | 0.12 | |
| Hydrogen Peroxide 3% | 1.55 | |
| Acetone | 0.40 | |
| Isopropanol 99% | 0.91 | |
| Kerasol TM | 5.65 | |
| Germaben II TM | 2.82 | C |
| Purified Water | 36.24 | |
| Dehyquart A | 1.00 | |
| Ammonium pH 9.0 Thioglycollate (60%) | 8.81 | D |
| Ammonia (28%) | 0.94% | |
| Kerasol TM | 2.82 | |
| Arlasolve 200 TM | 4.00% | E |
| Fragrance | 1.88 | |

Procedure: Agitate purified water (A) rapidly with "lightnin" mixer and sprinkle PVP K-30 slowly onto the surface. Allow PVP to go into solution. Add remainder of A ingredients and mix in well. Add B ingredients individually and mix well after each addition. Add C ingredients individually and mix in well after each addition. In a separate container add ammonium thioglycollate and use ammonia solution to bring the pH to 9.0. Add kerasol TM and mix in very well. Add this D phase to the batch and blend it in very well. In a separate container heat Arlasolve 200 TM very gently to liquify. Add remaining E ingredients separately and mix very well. Add this to the batch and mix until the produce is uniform.

| EXAMPLE VIII | | |
|---|---|---|
| Component | Weight Percent | |
| Purified Water | 41.91 | A |
| PVK-30 | 0.22 | |
| Lanogel 41 | 0.05 | |
| Propylene Glycol | 0.05 | |
| Brij 35 | 0.13 | |
| Essence of Rosemary | 0.33% | |
| Essence of Pimpernil | 0.33% | |
| Allantoin | 0.34% | |
| Glycerine | 0.16% | B |

| EXAMPLE VIII | | |
|---|---|---|
| Component | Weight Percent | |
| Citric Acid 5.88% | 0.04 | |
| Hydrogen Peroxide 3% | 0.52 | |
| Acetone | 0.13 | |
| Isopropanol 99% | 0.30 | |
| Kerasol TM | 1.88 | |
| Germaben II TM | 0.94 | C |
| Purified Water | 42.81 | |
| Ammonium pH 9.0 Thioglycollate (60%) | 2.95 | D |
| Ammonia (28%) | 0.09% | |
| Kerasol TM | 0.94 | |
| Arlasolve 200 TM | 4.00% | E |
| Fragrance | 1.88 | |

Procedure: Agitate purified water (A) rapidly with "lightnin" mixer and sprinkle PVP K-30 slowly onto the surface. Allow PVP to go into solution. Add remainder of a ingredients and mix in well. Add B ingredients individually and mix well after each addition. Add C ingredients individually and mix in well after each addition. In a separate container add ammonium thioglycollate and use ammonia solution to bring the pH to 9.0. Add kerasol TM and mix in very well. Add this D phase to the batch and blend it in very well. In a separate container heat Arlasolve 200 TM very gently to liquify. Add remaining E ingredients separately and mix very well. Add this to the batch and mix until the product is uniform.

| EXAMPLE IX | | |
|---|---|---|
| Component | Weight Percent | |
| Purified Water | 41.57 | A |
| PVP K-30 | 0.22 | |
| Lanogel 41 | 0.05 | |
| Propylene Glycol | 0.05 | |
| Brij 35 | 0.13 | |
| Biotin | 0.001 | |
| Elastin | 0.001 | |
| Glycerine | 0.16% | B |
| Citric Acid 5.88% | 0.04 | |
| Hydrogen Peroxide 3% | 0.52 | |
| Acetone | 0.13 | |
| Isopropanol 99% | 0.30 | |
| Kerasol TM | 1.88 | |
| Germaben II TM | 0.94 | C |
| Purified Water | 44.28 | |
| Ammonium pH 9.0 Thioglycollate (60%) | 2.95 | D |
| Ammonia (28%) | 0.09% | |
| Kerasol TM | 0.94 | |
| Arlasolve 200 TM | 4.00% | E |
| Fragrance | 1.75 | |

Procedure: Agitate purified water (A) rapidly with "lightnin" mixer and sprinkle PVP K-30 slowly onto the surface. Allow PVP to go into solution. Add remainder of A ingredients and mix in well. Add B ingredients individually and mix well after each addition. Add C ingredients individually and mix in well after each addition. In a separate container add ammonium thioglycollate and use ammonia solution to bring the pH to 9.0. Add kerasol TM and mix in very well. Add this D phase to the batch and blend it in very well. In a separate container heat Arlasolve 200 TM very gently to liquify. Add remaining E ingredients separately and mix very well. Add this to the batch and mix until the product is uniform.

| EXAMPLE X Concentrated Non-Perfumed Moisturizing Lotion | | |
| --- | --- | --- |
| Component | Weight Percent | |
| Arlamol E | 2.33 | A |
| Brij 72 | 8.93 | |
| Brij 78 | 2.25 | |
| Mineral Oil 70 | 19.89 | |
| Propylparaben | 0.31 | |
| Purified Water | 62.15 | B |
| Disodium EDTA | 0.16 | |
| Dimethicone | 0.16 | |
| Methylparaben | 0.70 | |
| Propylene Glycol | 2.33 | |
| Germaben II | 0.79 | C |

Procedure: Charge main mixing kettle with B ingredients and heat while mixing to 80°–85° C. In a separate container heat A ingredients to 80°–85° C. and mix until uniform. At 80°–85° C. add mixed A ingredients to mixed B ingredients while thoroughly mixing. Cool to 50°–55° C. At 50°–55° C. add Germaben and blend in very well. Continue to cool to 30° C. and use at this temperature.

| EXAMPLE XI | | |
| --- | --- | --- |
| Component | Weight Percent | |
| Concentrated Non-Perfumed Moisturizing Lotion (Ex. XII) | 8.85 | A |
| Purified Water | 56.94 | B |
| Elastin | 0.001 | |
| Biotin | 0.001 | |
| Carbopol 940 | 2.36 | |
| Concentrated Stock Sol'n Example VIII | 29.23 | C |
| Fragrance | 1.75 | D |
| Coloring Agent | 0.87 | E |

Procedure: This is a 4% Carbopol dispersion. Measure water and agitate at high speed. Add elastin and then biotin and allow them to disperse. Add Carbopol 940 to the lip of the vortex and mix well until the dispersion is complete. Add component A to the mixing kettle at 25°–30° C. and add B phase from above and mix until uniform. Add component C to mixture of A and B and mix until uniform. Add fragrance and coloring agent.

| EXAMPLE XII Non-Perfumed Moisturizing Lotion | | |
| --- | --- | --- |
| Component | Weight Percent | |
| Arlamol E | 1.36 | A |
| Brij 72 | 5.21 | |
| Mineral Oil 70 | 11.60 | |
| Propylparaben | 0.18 | |
| Purified Water | 77.4 | B |
| Disodium EDTA | 0.10 | |
| Dimethicone | 0.09 | |
| Methylparaben | 0.41 | |
| Propylene Glycol | 1.36 | |
| Dowicil 200 | 0.05 | C |
| Purified Water | 0.50 | |
| Formaldehyde 37% | 0.2 | D |
| Germaben II | 0.23 | E |

Procedure: Heat A phase components to 70°–75° C. and mix until uniform. Charge main kettle with water and begin heating to 70°–75° C. Add the remainder of phase B components and mix to dissolve the solids. Add, at 70°–75° C., A phase to B phase while mixing. Blend well and cool to 35°–40° C. Premix C phase and add to the batch when the solution is clear. Add D and E phases one at a time and mix in well. Cool to 25°–30° C. and use at this temperature.

| EXAMPLE XIII | | |
| --- | --- | --- |
| Component | Weight Percent | |
| Non-Perfumed Moisturizing Lotion (Ex. XIV) | 8.70 | A |
| Purified Water | 56.11 | B |
| Carbopol 940 | 1.15 | |
| Essence of Rosemary | 0.20 | |
| Essence of Althea | 0.20 | |
| Essence of Bilberry | 0.20 | |
| Essence of Jaborand | 0.20 | |
| Essence of Verbena | 0.20 | |
| Triethanolamine 99% | 2.60 | C |
| Concentrated Stock Sol'n Example VIII | 28.70 | D |
| Fragrance | 1.74 | E |

Procedure: In a separate mixing tank agitate water at high speed and spring Carbopol 940 onto the vortex. Disperse Carbopol and add remaining B phase components. Mix until carbopol dispersion is complete. Charge mixing tank with A component and hold at 25°–30° C. Add B mixture and blend until homogeneous. Add triethanolamine and mix in well until homogeneous. Add component D until homogeneous. Add component E and blend in well.

| EXAMPLE XIV STORAGE STABLE COMPOSITION | |
| --- | --- |
| Component | Weight Percent |
| Activated Protein | 0.1 to 12.0% |
| Reducing Agent | 0.1 to 15.0% |
| Antioxidant | 0.01 to 4.0% |
| Water, acids, bases buffering agents, emulsifying agents, thickeners, preservatives, organic solvents coloring agents, fragrance | 79.0 to 99.79% |

Procedure: From activated protein separately with solution containing reducing agent at a pH above about 9. Mix in remaining components until final mixture is homogeneous.

| EXAMPLE XV STORAGE STABLE COMPOSITION INCLUDING OXIDIZING AGENT | |
| --- | --- |
| Component | Weight Percent |
| Activated Protein | 0.1 to 12.0% |
| Reducing Agent | 0.1 to 15.0% |
| Oxidizing Agent | 0.001 to 4.0% |
| Antioxidant | 0.01 to 4.0% |
| Water, acids, bases buffering agents, emulsifying agents, thickeners, preservatives, organic solvents coloring agents, fragrance | 75.0 to 99.789% |

Procedure: Form activated protein separately with solution containing reducing agent at a pH above about 9. Mix in remaining components until final mixture is homogeneous.

EXAMPLES XVI-XXII (Wound Healing)

A 35 year old man who had a match stick to his finger upon lighting it applied the composition from Example I immediately to the wound. It left a black mark where the matchhead stuck to the skin. Within 10 minutes the pain disappeared. Within 18 hours it was as if there was no wound except for a small, dark skin discoloration.

There was no blistering, no tightening of the skin at the site, no pain and no loss or compromise in the use of the digit. Wound healing was greatly accelerated by the classical measures of "rubor, dolor and calor."

A 35 year old New York man cut the temporal aspect of the second phalange of his left index finger and applied the formulation of Example III immediately. The bleeding wound closed within 15 minutes and the bleeding stopped while several people observed it. They tried to separate the edges of the wound with their fingers at this time and could not. Clot retraction and reepithelialization were complete within 2 days with no sclerification. This healing process would have been expected to take 7 to 10 days otherwise.

A horse with a 3 year chronic history of a lower leg proud flesh wound (equine exuberant granulation) which was treated with many medications including systemic antibiotics, laser debulking and skin grafts to no avail, responded to the formulation of Examples I and IV. The initial lesion was about 3 inches in diamter. Following 3 months of therapy the granulation bed reepithelialized and the coat regrew. Skin function and appearance is completely restored. This horse is now back in jumping competition for the first time in 3 years. Three veterinarians who treated this horse did not expect the wound to ever resolve.

A dog was treated with the formulation of Example IV at the Oradell (N.J.) Animal Clinic with a Lick Granuloma of 2 years in duration. The condition had been treated by six vets previously to no avail. After thousands of dollars of diagnostics and treatment the formulation of Example IV was used, and the granuloma resolved. It is now covered with a thick skin, no longer weeps or bleeds, and is covered with a healthy coat. The animal no longer licks it. After a long and chronic course, the attending veterinarian did not expect this granulation to resolve. When it did resolve, both he and the owner of the dog call it "miraculous."

A St. Bernard with bilateral lick granulomas on its forepaws of 6 months duration had the formulation of Example II applied daily to one paw. Within 4 days the treated wound closed and stopped weeping and bleeding, while the untreated wound is unresolved. The owner of this dog, an experienced breeder and kennel owner said the response of this wound to the formulation was the most dramatic wound healing she had ever observed.

Two horses owned by different owners (one, a veterinarian) had hock injuries that were sutured dehised and reopened due to the continual flexion and tension at the hock. Both injuries were subacute and of 6 weeks and 9 weeks duration. Upon the initial application of the compound of Example II a dramatic improvement in both horses was evident within 12 hours. A clear acceleration of granulation bed formation, re-epithelialization and coat restoration was observed over what was expected. Both wounds closed and resolved within 14 days of daily therapy after not resolving for months previously despite being treated with standard therapy.

Veterinarians at the Meadowlands racetrack (N.J., USA) used the formulation of Example II for lower leg injuries in race horses and report greatly accelerated time to healing. Specifically, heal cracks and coronary band overreach injuries which are common in race horses responded by filling, re-epithelialization and regaining a normal appearance and function which does not limit their performance. This occurred within 5-15 days versus the customary three to eight weeks.

Examples XXIII-XXV (Hoof Wounds)

A New Jersey girl found her horse had a split hoof in January of 1988 which was not responsive to any therapy. This wound consisted of a split in the coronary band and the upper part of the hoof wall which exposed the sensitive tissues underneath. In May of 1988 the formulation of Example IV was applied daily. Within 2 weeks the wound was 90% healed as determined by hoof regrowth filling in the crack. Complete resolution took 4 weeks.

A horse at the U.S. Equestrian Team barns had kicked its foreleg with a rear leg and experienced an overrach injury to the cornary band which was expected to heal without treatment in 10-12 weeks. Using the formulation of Example IV daily initial healing as defined as a cessation of weeping and bleeding and a closing of the wound was observed in 3 days, and complete healing occurred within 10 days.

A horse with a hoof wound resulting in an evulsion which severed the front of the hoof wall completely as well as some of the underlying sensitive tissue wept and bled, and treatment with traditional therapies for 2 months was not adequate to stem the weeping and bleeding from the wound. Following initiation of daily therapy with the formulation of Example IV the wound stopped weeping and bleeding within 2 days. Healing progressed at a greatly accelerated rate, and at 2 weeks the sensitive underlying tissues had stabilized. At the end of a 3 month period of daily application this hoof is completely healed and indistinguishable from the other hooves on the horse.

Examples XXVI-XXVIII (Itching and Rashes)

A New York dermatologist with a chronic history of a full scalp cap of sebborhea characterized by itching and dandruff, which was not responsive to any therapy completely responded to the forrmulation of Example I within 1 week of daily applications. Itching ceased within 2 days after initiating therapy. The characteristic exudate stopped as did flaking of the scalp. Continued daily applications of this formulation has completely resolved his condition.

A dog with a history of ideopathic chronic itching which was not resolved by any medication or biweekly bathing was treated with a single application of this formulation and the itching resolved. It is speculated that subsequent applications may be necessary, but have not been needed at the time of this writing, which is 3 weeks after the initial application.

A horse with a history of tail rubbing (resulting in hair loss) which began, presumably, as a result of worms but persisted despite effective deworming was treated with a single application of this compound following a 2 week episode of tail rubbing subsequent to effective deworming. The tail rubbing immediately stopped, no further treatment was required, and the tail hair grew back in. Tail rubbing is not uncommon in horses. No one knows why they do it, and heretofore there was no effective therapy to treat it.

Example XXIX (Rashes)

Dog had a severe pyoderma with hair loss, oozing and bleeding, and itching resulting in self-inflicted lacerations of over 1 year duration. Suspected IgA deficiency. Two weeks of lincomycin almost a year earlier provided a slight positive effect but was discontinued due to toxicity. In late, 1987 thyroid supplementation was tried without results. Euthanasia was considered. In the middle of 1988, experimental treatment with the composition from Example VIII was initiated. Within 4 days all open sores scabbed over. Within 8 days all lesions healed with appreciable hair growth. Within 21 days the dog was approximately normal in appearance. Complete hair regrowth over the entire body has begun. After 3 months, the dog is completely restored. No more deficits, self-mutilation, etc. The treatment was stopped and the problem seems to be completely and permanently resolved. There has been no loss of hair since ceasing treatment.

Example XXX (Wound Healing)

A cat had a radial nerve paralysis resulting in a forelimb dragging which caused a chronic hair loss and abrasion. The underlying wound was several years old. Treatment with the composition of Example VIII resulted in the wound closing within days and the growing of fur over a 10 day period

Example XXXI (Flea Bites)

Flea bite allergic reactions in dogs cease immediately upon application. Usually a Shar-pei gets 1" bald, raised inflamed area when bit. Dramatic decrease in flea allergy response in Shar-pei, St. Bernard and Seskie Terrier using the composition of Example VIII.

Example XXXII (Wound Healing)

The composition of Example VIII sealed a hole in two-three weeks in the cheek of a foal which could not be sutured.

Example XXXIII (Wound Healing)

A horse stepped upon a stub of a metal fence post and had a 3" wide puncture going down to the tendons. After application of the composition of Example VIII, the wound healed quickly with no "proud flesh" occurring.

Example XXXIV (Lick Granuloma)

A 14 year old doberman had a 7 year history of "lick granuloma." 3 small animal vets recommended amputation. Dog got progressively worse until the point was reached where the dog could not even walk. Euthanasia was considered. The composition of Example VIII was applied to the condition. After two months of treatment the dog walked. After two and one half months the dog was running, which had not occurred in years.

Examples XXXV and XXXVI (Resolution of Existing Acne Scars)

A 29 year old female stock broker used a daily application of the composition of Example V and within two months noticed her acne scars had significantly decreased in size.

A 36 year old housewife utilizing the composition of Example V noticed an improvement in existing acne pitting within a month of daily application.

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the inventions' those of skill in the art will readily understand. Accordingly, such variations and modifications are considered to be within the purview and scope of the invention and the following claims.

What is claimed is:

1. A method for treating abnormal or damaged conditions of the epithelium, including skin, and ungual tissue comprising applying to the affected area a composition comprising:
   a). about 0.01 to about 12% by weight of a protein containing sufficient cysteinyl groups to covalently bind said protein to said tissue;
   b). about 0.1 to about 15% by weight of a reducing agent capable of reducing cystine to cysteine in said protein;
   c). about 0.001 to about 4.0% by weight of an oxidizing agent capable of oxidizing cysteine to cystine; and
   d). about 81.0% to about 99.889% by weight of at least one component selected from the group consisting of water, acids, bases, buffering agents, emulsifying agents, thickeners, solvents, preservatives, coloring agents and perfuming agents.

2. The method according to claim 1 wherein said protein is a keratin protein.

3. The method according to claim 1 wherein said reducing agent is a salt of thioglycollic acid.

4. The method according to claim 3 wherein said reducing agent is ammonium thioglycollate.

5. The method according to claim 2 wherein said oxidizing agent is selected from the group consisting of sodium perborate and hydrogen peroxide.

6. The method according to claim 5 wherein said oxidizing agent comprises about 0.001 to about 1.5% by weight of said composition.

7. The method according to claim 6 wherein said oxidizing agent is hydrogen peroxide.

8. The method according to claim 1 wherein said protein is a keratin protein, said reducing agent is ammonium thioglycollate and said oxidizing agent is hydrogen peroxide.

9. The method according to claim 1 wherein said condition is dandruff.

10. The method according to claim 1 wherein said condition is sebborhea.

11. The method according to claim 1 wherein said condition is canine cutaneous granuloma.

12. The method according to claim 1 wherein said condition is equine exuberant granuloma.

13. A method for treating abnormal or damaged conditions of the epithelium including skin, and ungual tissue comprising applying to the affected area a composition comprising:
   a). about 0.01 to about 12% by weight of a protein containing sufficient cysteinyl groups to covalently bind said protein to said tissue;
   b). about 0.1 to about 15% by weight of a reducing agent capable of reducing cystine to cysteine in said protein; and
   c). about 81.0% to about 99.889% by weight of at least one component selected from the group consisting of water, acids, bases buffering agents, emulsifying agents, thickeners, solvents, preservatives, coloring agents and perfuming agents.

14. The method according to claim 13 wherein said protein is a keratin protein.

15. The method according to claim 13 wherein said reducing agent is ammonium thioglycollate.

16. The method according to claim 13 wherein said protein is a keratin protein and said reducing agent is ammonium thioglycollate.

17. The method according to claim 13 wherein said condition is dandruff.

18. The method according to claim 13 wherein said condition is sebborhea.

19. The method according to claim 13 wherein said condition is canine cutaneous granuloma.

20. The method according to claim 13 wherein said condition is equine exuberant granuloma.

21. A composition for treating acne comprising:
 (a) about 0.01 to about 12% by weight of a protein containing sufficient cysteinyl groups to covalently bind to the skin or scalp;
 (b) about 0.1 to about 15% by weight of a reducing agent capable of reducing cystine to cysteine in said protein;
 (c) at least about 73% by weight of at least one component selected from the group consisting of water, bases, acids, buffering agents, emulsifying agents, thickeners, coloring agents and perfuming agents; and
 (d) an effective amount of an anti-acne agent.

22. The composition according to claim 21 wherein said anti-acne agent is selected from the group consisting of benzoyl peroxide and tetracycline.

23. The composition according to claim 21 further comprising an oxidizing agent.

24. The composition according to claim 21 further comprising a volatile antioxidant.

25. A composition for treating wounds and damaged conditions of the epithelium, including skin comprising:
 (a) about 0.01 to about 12% by weight of a protein containing sufficient cysteinyl groups to covalently bind to a wounded area or the skin selected from the group consisting or ribonuclease T1, human serum albumin, and fibrinogen and its derivatives;
 (b) about 0.1% to about 15% by weight of a reducing agent capable of reducing cystine groups to cysteine groups; and
 (c) about 73% to about 99.98% by weight of at least one component selected from the group consisting of water, bases, acids, buffering agents, emulsifying agents, thickeners, coloring agents and perfuming agents.

26. A method for diminishing the effects of acne scars in the skin comprising applying to the scarred area a composition comprising:
 a). about 0.01 to about 12% by weight of a protein containing sufficient cysteinyl groups to covalently bind said protein to the skin;
 b). about 0.1 to about 15% by weight of a reducing agent capable of reducing cystine to cysteine in said protein; and
 c). about 81.0% to about 99.889% by weight of at least one component selected from the group consisting of water, acids, bases, buffering agents, emulsifying agents, thickeners, solvents, preservatives, coloring agents and perfuming agents.

27. The method according to claim 26 wherein said protein is a keratin protein.

28. The method according to claim 27 wherein said reducing agent is ammonium thioglycollate.

29. The method according to claim 28 wherein said protein is a keratin protein and said reducing agent is ammonium thioglycollate.

30. The method according to claim 29 wherein said composition further comprises about 0.001 to about 4.0% by weight of an oxidizing agent capable of oxidizing cysteine to cystine in said protein.

31. The method according to claim 13 wherein said composition further includes a volatile antioxidant.

32. The method according to claim 31 wherein said composition further includes an effective amount of an oxidizing agent capable of oxidizing cysteine to cystine.

33. The method according to claim 1 wherein said condition is selected from the group consisting of wounds, sebborhea, psoriasis, dandruff, acne, scars, callouses, corns, burns, rashes, dermatitis, equine exuberant granuloma, decubitis ulcers, and canine cutaneous granulomas.

34. The method according to claim 13 where in said condition is selected from the group consisting of wounds, sebborhea, psoriasis, dandruff, acne, scars, callouses, corns, burns, rashes, dermatitis, equine exuberant granuloma, decubitis ulcers, and canine cutaneous granulomas.

* * * * *